United States Patent
Schmieding et al.

(10) Patent No.: US 6,780,115 B2
(45) Date of Patent: Aug. 24, 2004

(54) METHOD AND SYSTEM FOR INTRAOPERATIVELY REVISING THE LENGTH OF FRACTURE FIXATION SCREWS

(75) Inventors: Reinhold Schmieding, Naples, FL (US); Karen L. Gallen, Naples, FL (US)

(73) Assignee: Arthrex, Inc., Naples, FL (US)

( * ) Notice: Subject to any disclaimer, the term of this patent is extended or adjusted under 35 U.S.C. 154(b) by 47 days.

(21) Appl. No.: 10/163,303

(22) Filed: Jun. 7, 2002

(65) Prior Publication Data

US 2003/0229354 A1 Dec. 11, 2003

(51) Int. Cl.$^7$ .............................. B21H 3/02; A61B 17/56
(52) U.S. Cl. .............................. 470/10; 606/72; 606/73; 606/86; 606/102
(58) Field of Search .............................. 606/60, 62, 65, 606/72, 73, 76, 77, 79, 86, 102; 408/99; 11/101; 470/10, 57, 50, 65, 66, 67, 68, 69, 80, 84, 185, 184, 187, 188

(56) References Cited

U.S. PATENT DOCUMENTS

| | | | |
|---|---|---|---|
| 1,640,942 A | * | 8/1927 | Johnson ...................... 408/159 |
| 2,494,229 A | * | 1/1950 | Collison ...................... 606/73 |
| 4,405,267 A | * | 9/1983 | Stoken ...................... 408/101 |
| 4,759,670 A | | 7/1988 | Linder et al. |
| 4,869,242 A | | 9/1989 | Galluzzo |
| 4,940,467 A | | 7/1990 | Tronzo |
| 5,062,843 A | | 11/1991 | Mahony, III |
| 5,180,388 A | | 1/1993 | DiCarlo |
| 5,609,595 A | | 3/1997 | Pennig |
| 5,824,247 A | * | 10/1998 | Tunc ........................... 264/135 |
| 5,997,538 A | | 12/1999 | Asnis et al. |
| 6,019,762 A | | 2/2000 | Cole |
| 6,155,756 A | * | 12/2000 | Mericle et al. ............... 409/66 |
| 6,302,887 B1 | * | 10/2001 | Spranza et al. ............... 606/73 |
| 6,551,323 B2 | * | 4/2003 | Doubler et al. ............... 606/73 |
| 6,579,293 B1 | * | 6/2003 | Chandran ..................... 606/64 |

* cited by examiner

*Primary Examiner*—Ed Tolan
(74) *Attorney, Agent, or Firm*—Dickstein Shapiro Morin & Oshinsky, LLP

(57) ABSTRACT

The length of a bone fracture fixation screw may be intraoperatively adjusted with the aid of a cutting jig that includes a measuring block which is slidable along a rail adjacent a measuring scale and a holding block to facilitate cutting the distal end of the screw once the desired length has been determined. A tip sharpener may be incorporated into the cutting jig or may be provided separately, for reforming a point at the distal tip of the cut fixation screw. A method of bone fracture fixation includes selecting an appropriately sized fixation screw, drilling a hole across the fracture site, forming a countersunk hole across the drilled hole, measuring the depth of the drilled hole to determine the length of screw needed, tapping the entire length of the drilled hole or the only the distal fragment when the lag technique is used, placing the fixation screw into the cutting jig, setting the cutting jig to the measured length, cutting off any excess length from the distal end of the screw, inserting the end of the cut fixation screw into the sharpener, turning the screw until a pointed tip has been reformed at the distal end, and driving the screw into the drilled hole until the screw head is flush or countersunk with the surface of the bone.

20 Claims, 17 Drawing Sheets

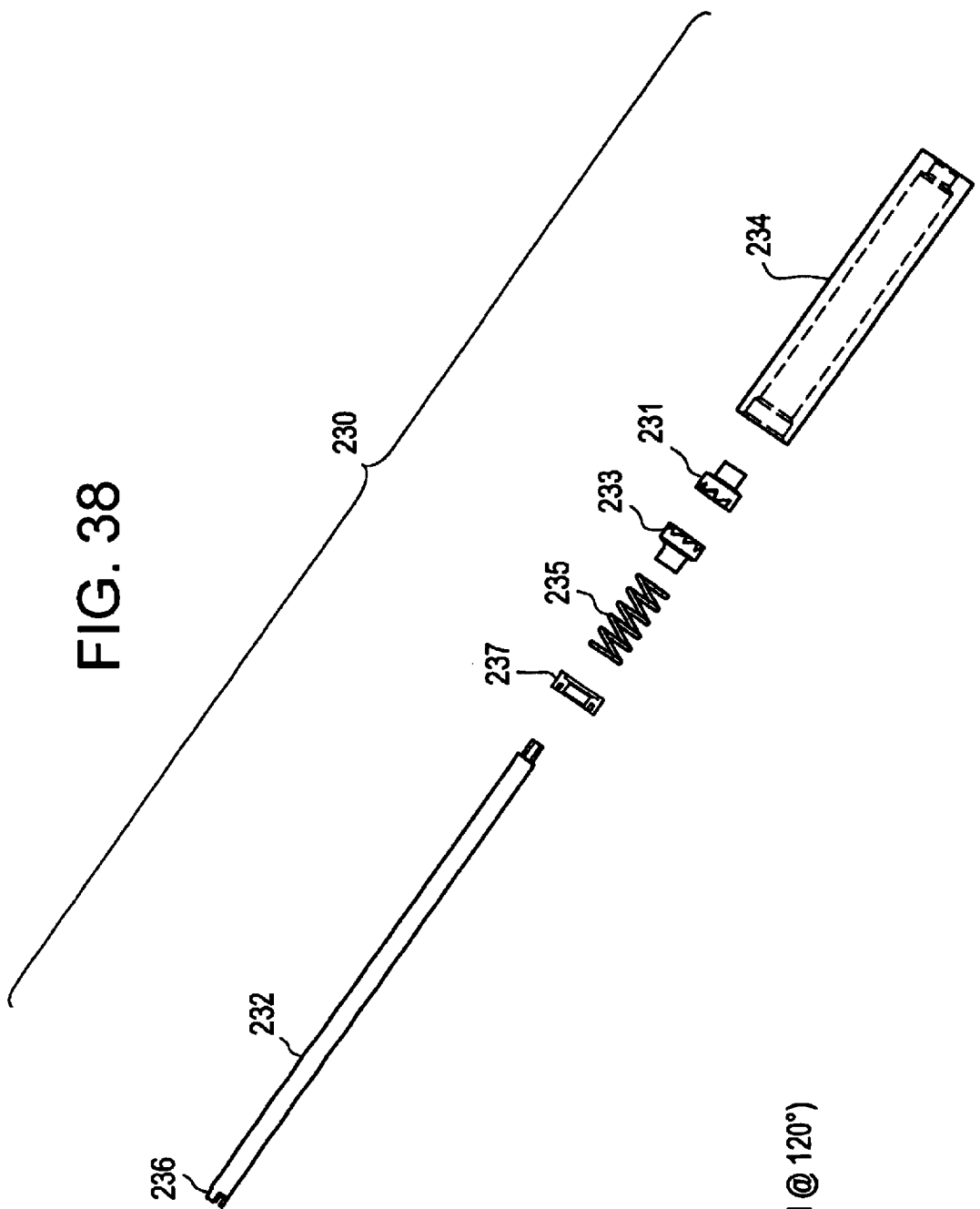
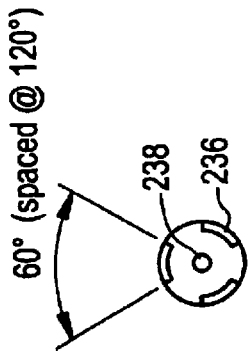

METHOD AND SYSTEM FOR INTRAOPERATIVELY REVISING THE LENGTH OF FRACTURE FIXATION SCREWS

BACKGROUND OF THE INVENTION

1. Field of the Invention

The present invention relates to a method of intraoperatively sizing a fracture fixation screw to a desired length, and a measuring and cutting system therefor.

2. Brief Description of the Related Art

When a patient suffers an injury in which a bone is fractured or fragmented, the injury often must be repaired by securing the bone fragments together with fixation elements such as pins and/or screws. The fixation elements may be removed after the bone fragments have fused back together, or alternatively they may be left in place permanently or until they are ultimately absorbed into the patient's body if the fixation elements are made of a bioabsorbable material.

A surgeon may choose to use either pins or screws or a combination of both to hold the bone fragments together, depending on the size of the fragments and the fixation strength necessary or desired to hold the fragments together. For example, screws provide greater fixation strength and greater pullout strength than pins, but pins may be more useful for securing smaller bone fragments in which the generally wider diameters of screws may risk further damaging the fragments. Where appropriate, however, screws are preferred over pins because of the advantages of greater fixation strength and greater pullout strength as mentioned above.

When fixation screws are to be used, it is typically necessary for the surgeon to have all sizes of the fixation screws on hand at the time of the surgery, unless a particularly experienced surgeon can identify beforehand a more limited size selection (diameter and/or length) of fixation screws to have available for the procedure. This usually requires that the surgeon have available for each surgery a complete set of screws containing screws of every diameter and every length which may be encountered in any fracture fixation procedure. Of course, it is very costly and cumbersome to provide such a large number fixation elements for each procedure, both for the manufacturer to produce the fixation screws in many different lengths and diameters, and for the surgeon or medical facility to purchase and store all of the fixation screws in every available length and diameter.

During the surgery, the surgeon selects the length and diameter of each screw to be installed based upon the size of the bone fragments to be secured together and the depth of the hole drilled for the fixation element. In drilling the hole and selecting the screw, the surgeon generally takes into consideration that the larger the diameter of the fixation screw, the greater the fixation strength provided to the bone. However, if screws having diameters which are too large are used, there is a risk of damaging or further splitting the bone fragments. The length of the screw is selected to accommodate the depth to which the fixation screw is to be inserted, and so that the head of the screw after installation does not sit above the bone surface, as this will interfere with proper healing, among other undesirable effects.

In the event that fixation pins are to be used, it may also be necessary for the surgeon to have pins in a variety of different diameters available in the operating room during surgery. Here, however, several types of pins are known in the prior art in which the length of the pin may be adjusted by the surgeon after insertion into the bone. For example, U.S. Pat. No. 4,869,242 to Galluzzo and U.S. Pat. No. 5,180,388 to DiCarlo each discloses a bone fixation pin in which, after installation into the bone, the protruding portions of the pins are broken off or cut, respectively. The smooth shafts and relatively thin diameters render the fixation pins readily amenable to such revisions after installation.

Other types of fixation devices in which the length may be adjusted intraoperatively are disclosed in U.S. Pat. Nos. 5,997,538 and 6,019,762 to Asnis et al., and Cole, respectively. Asnis discloses a ratcheting bone screw kit which includes a body for penetrating into bone tissue, a screw shaft having a unidirectional stop, a fastening element matingly configured to receive the shaft and which advances in a ratcheting manner along the shaft when rotated relative to the shaft. Similarly, Cole discloses a fixation device comprising a shaft and a head engageable with the shaft and moveable between a first and second position. These devices are each rather complex, Asnis in particular, having several physically distinct and cooperating parts and in which the excess length of one part must also be cut after installation of the device.

Given the superior fixation strength achievable by using fixation screws for bone fracture fixation, it would be desirable if the lengths of fixation screws could be revised instraoperatively without the necessity for a complex arrangement of cooperating parts in the fixation device.

SUMMARY OF THE INVENTION

The present invention addresses the needs of the prior art by providing a method and system for intraoperatively revising fixation screws used for bone fracture fixation. Specifically, the invention encompasses a device or devices for intraoperatively measuring and cutting bone fracture fixation screws to desired lengths and for re-sharpening the tip of each cut fixation screw, a method for performing the revision technique, and a method for performing a bone fracture fixation procedure.

The fracture fixation screws are preferably bicortical bioabsorbable screws having a constant diameter shaft and a low profile head. The shaft may be fully threaded or partially threaded and have a tapered/pointed distal tip. Preferably, the screws are provided in a standard length but in a variety of diameters. Washers may be attachable to the head of each fixation screw to provide additional compression, or if any sutures are used in the repair, for securing the sutures around the fixation screw. The washers may have a rounded upper surface and a bottom surface suitable for resting on the bone surface around the hole into which the fixation screw is inserted, or may alternatively have a flat upper surface and a rounded bottom for resting in a counterbore surrounding the hole into which the fixation screw is inserted.

The length of the screws may be adjusted during a fracture fixation operation with the aid of a cutting jig that includes a measuring block which is slidable along a rail adjacent a measuring scale and a holding block to facilitate cutting the distal end of the screw once the desired length has been determined. A tip sharpener may be incorporated into the cutting jig or may be provided separately, for reforming a point at the distal tip of the cut fixation screw.

A preferred method according to the present invention includes selecting an appropriately sized fixation screw to be installed; drilling a hole across the fracture site using an appropriately sized drill bit; forming a countersunk bore across the drilled hole; inserting a measuring tool into the drilled hole to determine the length thereof; tapping either the entire length of the drilled hole or only the distal fragment thereof when the lag technique is to be performed; placing the selected fixation screw into a cutting jig; setting the cutting jig to a measurement corresponding to the measured length of the drilled hole; if the selected fixation screw is longer than the measurement set in the cutting jig; cutting off the excess length from the distal end of the screw; inserting the distal end of the cut fixation screw into the sharpener; turning the screw until a pointed tip has been re-formed at the distal end of the screw; aligning the revised screw with the drilled hole; engaging the revised screw with an appropriately sized driver; and advancing the screw into the drilled hole using the driver until the head of the screw is flush or countersunk with the surface of the bone.

Other features and advantages of the present invention will become apparent from the following description of the invention, which refers to the accompanying drawings.

BRIEF DESCRIPTION OF THE DRAWINGS

FIG. 38 is an exploded view of a torque limiting driver usable in conjunction with the present invention.

FIG. 39 is a distal end view of the driving shaft shown in FIG. 38.

DETAILED DESCRIPTION OF THE PREFERRED EMBODIMENTS

Figure 1:
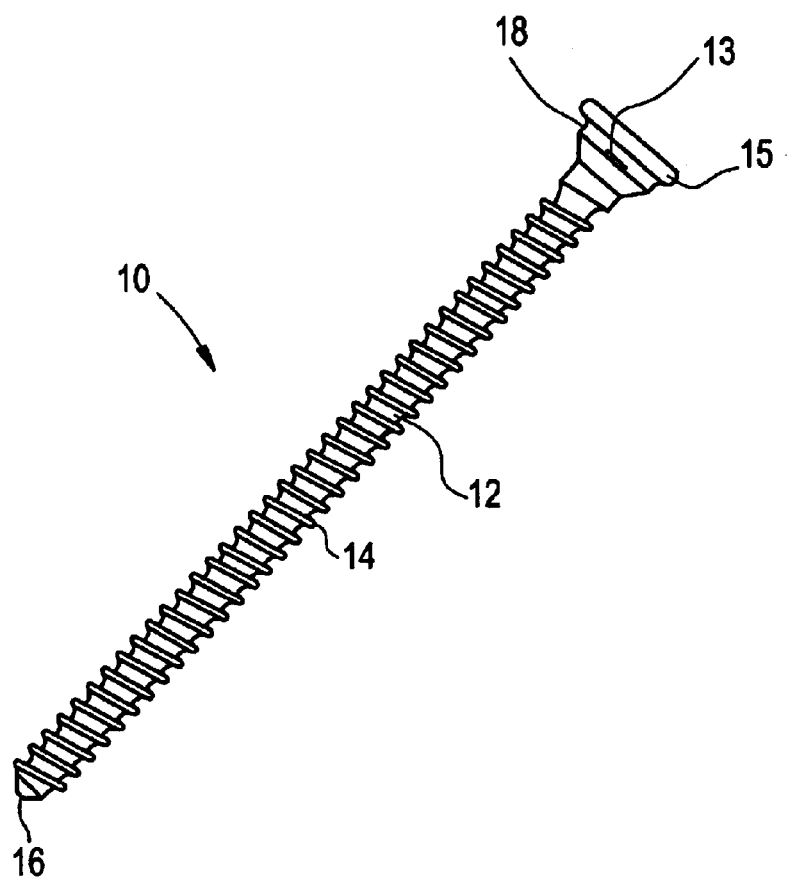
FIG. 1 is an elevational view of a first preferred embodiment of a bone fracture fixation screw usable in connection with the present invention.

A first preferred embodiment of a fracture fixation screw usable in connection with the present invention is shown in FIG. 1. As shown, fixation screw 10 includes a main body 12 having a continuous thread 14 and a sharpened point at its distal end 16, a neck portion 18 and a head 15 at the proximal end thereof.

Figure 3:
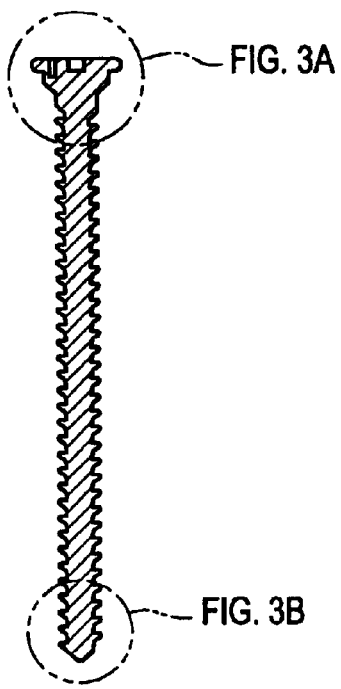
FIG. 3 is a cross-sectional view of the fixation screw through the plane III—III in FIG. 2.
Figure 3A:
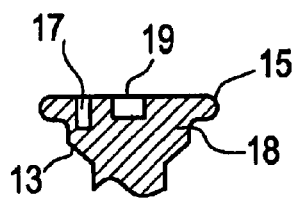
FIG. 3A is an enlargement of the upper circled region of FIG. 3.
Figure 3B:
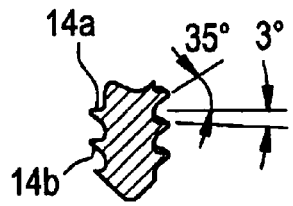
FIG. 3B is an enlargement of the lower circled region of FIG. 3.

Fixation screw 10 may be provided in a variety of sizes, including, but not limited to screws having a major diameter of approximately 2.7 mm, 3.5 mm, 4.5 mm, 4.0 mm and 6.5 mm. In these exemplary sizes of the fixation screw 10, the preferred shaft lengths are respectively 24 mm, 40 mm, and 70 mm having cortical threads, and 50 mm and 110 mm having cancellous threads. Also, as illustrated in FIG. 3B, the angle between the distal surface 14b of each thread flight and the proximal surface 14a of the next thread flight in the distal direction is between approximately 30° to 40°. Of course, it should be understood that the fixation screws of the types described herein may be manufactured or provided in additional or alternative sizes. Moreover, the fixation screws exemplified herein may be provided having different measurements for any one or more of the dimensions mentioned above.

The tapering of the point at the distal tip 16 forms approximately a 45° with the vertical (longitudinal) axis "a" through the length of the screw. The thread 14 includes a gradual runout for approximately 2–3 flights at the proximal portion of the main body 12 just distally of neck portion 18.

Neck portion 18 is formed between head 15 and main body 12, and correspondingly, has a diameter slightly greater than the major diameter of body 12 and less than that of head 15. The height of neck portion 18 corresponds to the thickness of the washers that may be attached to the screw, if desired, as will be described below. Neck portion 18 also has elongated bumps 13 (FIGS. 1, 3A) formed on the radial surface of neck portion 18. Preferably, there are two elongated bumps spaced 180° apart around neck portion 18. The function of bumps 13 will be described in detail further below.

Head 15 is generally formed as a flat disc attached to neck portion 18, and may range from approximately 5 to 10 mm in diameter, depending on the size (diameter) of the screw. Head 15 has a smooth, low profile, about from 1.0 to 1.5 mm thick, to minimize trauma to surrounding tissue. The proximal face of head 15 includes a central bore 19 about 1 to 2 mm deep, depending on the size of the screw, for engaging a driver or a measuring block on a cutting jig as will be described later. Optionally, instead of a central bore 19 having a limited depth, fixation screw 10 may be cannulated throughout its entire length.

Figure 2:
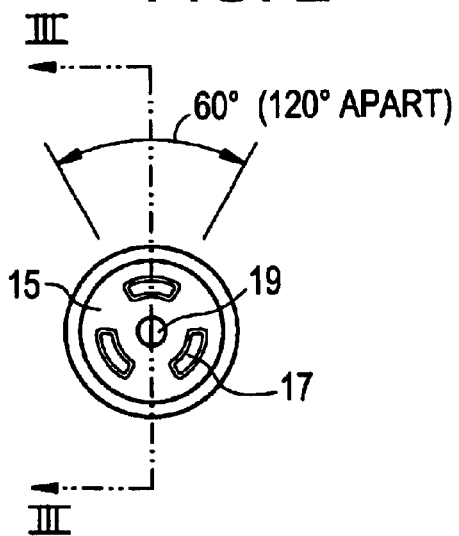
FIG. 2 is a proximal end view of the fixation screw shown in FIG. 1.

Head 15 also has at least one opening on its proximal face for engaging a driver. Although many different drive coupling arrangements are possible, the preferred embodiment of the invention has three equally spaced arcuate slots 17 formed in the disk-shaped head, as shown in FIG. 2, to engage the driver used for delivery and installation of the fixation screw (to be described below). Slots 17 are formed in the central portion of head 15 which overlaps above neck portion 18, so that the depth of slots 17 can extend slightly below the depth of head 15 and into neck portion 18, as can be seen in FIGS. 3 and 3A, to enable solid coupling between an engaged driver and the screw for driving the same.

The screw is preferably formed of a bioabsorbable, biocompatible material, such as Resomer L210 Poly (L-Lactide) acid (PLLA) or an equivalent material, and is suitable for use for bone fracture fixation in the upper and lower extremities. In addition to being biocompatible and bioabsorbable, constructing the fixation screw from PLLA provides the advantages of not being visible on radiographs, and not interfering with MRI or CT scans. Moreover, such material renders the screw strong enough to provide a fixation strength of approximately 1000 N and 90° shear force. Most significantly, however, the PLLA material allows the screw to be easily cut to a desired length according to the method and using the system of the present invention.

Figure 4:
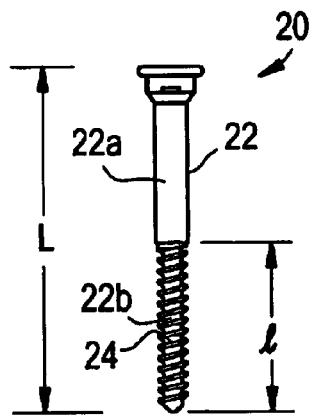
FIG. 4 is an elevational view of a second preferred embodiment of a bone fracture fixation screw usable in connection with the present invention.

A second preferred embodiment of the fracture fixation screw 20 is shown in FIG. 4. Fixation screw 20 is similar to fixation screw 10 of the first embodiment except that the screw body 22 does not have threads along an upper portion thereof. Instead, upper portion 22a of screw body 22 is smooth and has a diameter corresponding to the outer diameter of the threads 24 at the bottom portion of screw body 22b. The reason for non-threaded upper portion 22a will be discussed later.

Fixation screw 20 is preferably provided in 3.5 mm, 4.5 mm and 6.5 mm diameters, although additional sized are contemplated. Among screws of each diameter, additional sizes may be provided with varying ratios of total screw length to threaded lower body portion length. For example, the 3.5 mm screw may be provided with total length "L"/threaded lower portion length "l" measurements of 16 mm/10 mm, 24 mm/11 mm, 32 mm/12 mm, 38 mm/14 mm, and 45 mm/20 mm. Similarly, the 4.5 mm screw may be provided with total length "L"/threaded lower portion length "l" measurements of 35 mm/17 mm, 45 mm/17 mm, 55 mm/20 mm, 65 mm/23 mm, and 70 mm/23 mm, while the 6.5 mm screw may be provided with 65 mm/32 mm, 80 mm/32 mm, 95 mm/63 mm, and 110 mm/32 mm measurements. Other features and characteristics of fixation screw 20 are the same as discussed above with respect to fixation screw 10 shown in FIG. 1.

Fixation screw 10, 20 may be used in conjunction with a washer such as those shown in FIGS. 5–10, to increase the compression strength achieved by the fixation screw for holding the bone fragments together. When sutures are also used in the operation in conjunction with or in the proximity of the fixation screw, a washer may also be used to secure suture knots and/or the ends thereof.

The washers usable in conjunction with the fixation screws described herein can be fitted and retained around the neck portion 18 so that the washer is horizontally stable, yet can be rotated freely with respect to the fixation screw 10, 20. To achieve this arrangement, the inner diameter of the washer is only slightly larger than the diameter of neck portion 18 so as to enable the washer to be rotated easily, without friction, around the screw while preventing the washer from tilting and shifting loosely around the neck portion 18.

Figure 5:
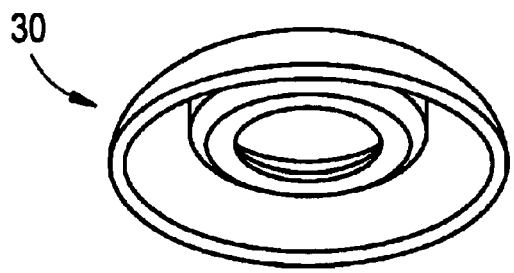
FIG. 5 is a distal perspective view of a first embodiment of a washer usable in conjunction with the fixation screws in the present invention.
Figure 6:
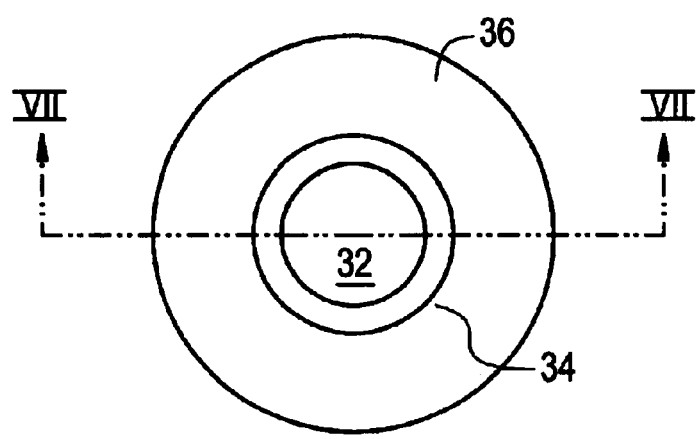
FIG. 6 is a top elevational view of the washer shown in FIG. 5.
Figure 7:
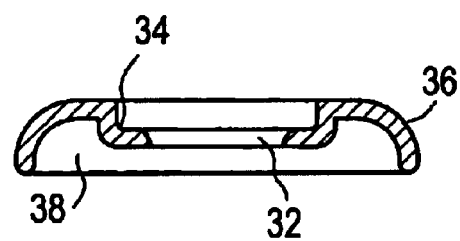
FIG. 7 is a cross-sectional view of the washer across the plane VII—VII in FIG. 6.

A first preferred embodiment of the washer that can be fitted onto the fixation screw is illustrated in FIGS. 5–7. The cap-shaped washer 30 may have an outer diameter in the range of approximately 10 mm to approximately 16 mm and a central opening 32 slightly larger in diameter than the diameter of the neck portion 18, 28 of the correspondingly sized screw onto which the washer may be fitted. Washer 30 also includes a ledge 34 formed around the inner peripheral surface of washer 30 for seating the screw head 15 thereon, and a cap-shaped outer portion 36 rising above the level of and surrounding the seating ledge 34.

Figure 11:
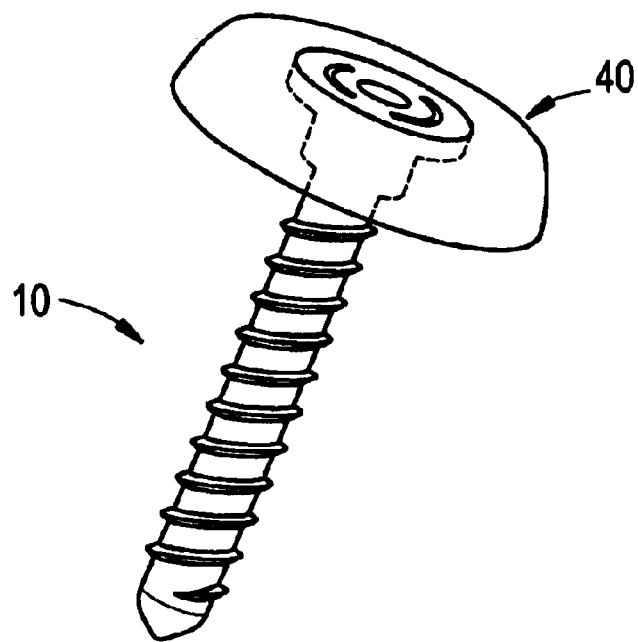
FIG. 11 shows the fixation screw of FIG. 1 in an assembled state with the washer shown in FIG. 5.

Cap-shaped outer portion 36 is shaped such that when washer 30 is positioned around the neck portion 18, the proximal surface of screw head 15 is substantially flush with the curved proximal surface of the cap-shaped outer ring 36 (as seen in FIG. 11). The cap-shaped outer portion 36 forms a space 38 (FIG. 7) under its curved surface for covering suture ends and knots tied around the periphery or the vicinity of the fixation screw. Thus, in addition to the added compression strength achievable with the fixation screw, cap-shaped washer 30 also provides the further advantage of eliminating potential irritation to surrounding soft tissue incurred by any suture knots formed in the vicinity during the operation.

Figure 8:
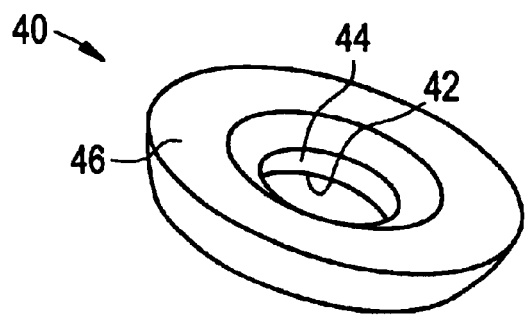
FIG. 8 is a proximal perspective view of a second embodiment of a washer usable in conjunction with the fixation screws in the present invention.
Figure 9:
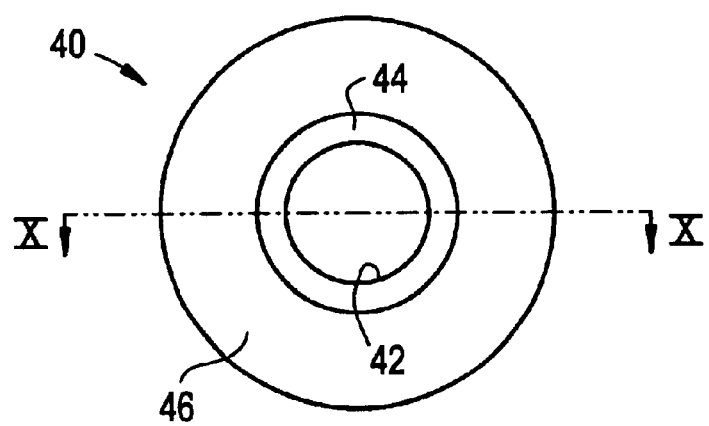
FIG. 9 is a top elevational view of the washer shown in FIG. 8.
Figure 10:
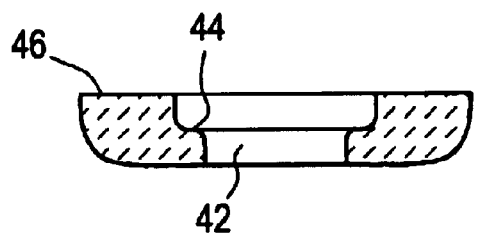
FIG. 10 is a cross-sectional view of the washer across the plane X—X in FIG. 9.
Figure 12:
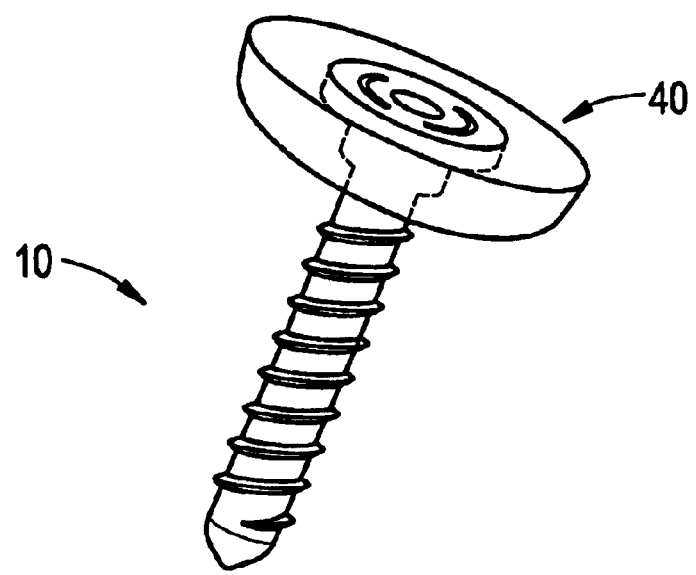
FIG. 12 shows the fixation screw of FIG. 1 in an assembled state with the washer shown in FIG. 8.
Figure 13:
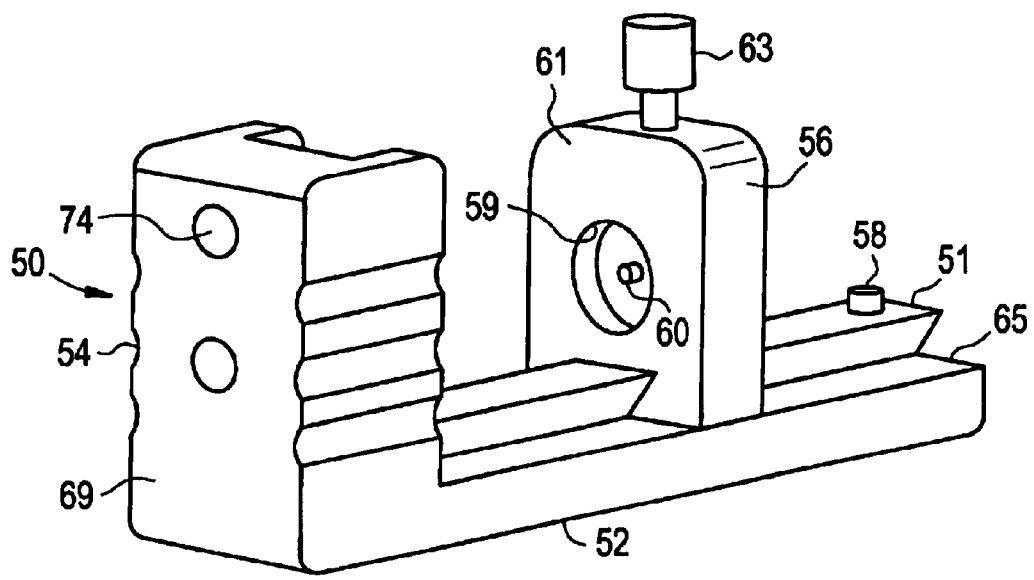
FIG. 13 is a distal perspective view of a first preferred embodiment of a cutting jig in accordance with the present invention.

FIGS. 8–10 illustrate a second preferred embodiment of the washer usable in conjunction with the fixation screws described herein. Cup-shaped washer 40 has a central opening 42 for receiving the fixation screw 10, 20 therethrough, a ledge 44 (FIG. 10) formed around the inner peripheral surface of washer 40, an outer peripheral portion 46 encircling ledge 44. The inner and outer diameters of washer 40 are substantially the same as with washer 30 shown in FIGS. 5–7, which may vary according to the size of the fixation screw onto which the washer may be attached. Outer portion 46 has a relatively flat upper surface at a height greater than that of ledge 44, and a cup-shaped bottom surface for resting in a counterbore formed around the hole into which a fixation screw to which the washer is attached is inserted. As shown in FIG. 12, when the washer 40 is positioned around the neck portion 18, head 15 of the fixation screw is seated on ledge 44 such that the proximal surface of screw head 15 is substantially flush with the proximal surface of outer portion 46.

The selected washer is fitted onto the neck portion 18 of the fixation screw by inserting the distal end of the screw through the central opening of the washer from the top side thereof, and raising the washer relative to the screw. The diameter of neck portion 18 is augmented slightly by the presence of elongated bumps 13 to thereby correspond with the inner diameter of the washer, so that friction is encountered when the washer is raised on the screw to this position. By pressing the two pieces together with additional pressure, the washer can be forced over the bumps and snapped into place around neck portion 18 above the elongated bumps 13 and below the head 15 of the fixation screw. Between elongated bumps 13 and the bottom surface of head 15, neck portion 18 has a height at least equal to the thickness of the washer at the inner diameter thereof. The washer is thus retained in position surrounding head 15 by the elongated bumps 13 and prevented from slipping off of neck portion 18.

The length of the fixation screws 10, 20 described above may be adjusted intraoperatively by a surgeon performing a bone fracture fixation procedure, using a cutting jig assembly in accordance with the present invention. Preferably, for best results, a different cutting jig assembly is provided for each diameter size of fixation screw. A first preferred embodiment of such a cutting jig 50 is discussed below with reference to FIGS. 13–24, while a second preferred embodiment of the cutting assembly 80 will be discussed with reference to FIGS. 25–30, and a third preferred embodiment of the cutting assembly will be discussed below with reference to FIGS. 31–34.

Cutting jig 50 generally includes a base member 52, a mounting block 54, and a measuring block 56. Base member 52 includes a rail 51 formed on the upper surface 67 thereof and extending centrally along the length of base member 52. Measuring block 56 is mounted on base member 52 and slidable along rail 51 for positioning a fixation screw to be cut to a desired length.

Figure 18:
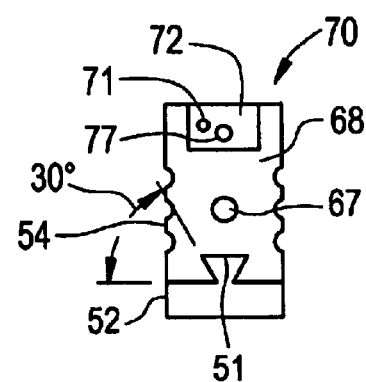
FIG. 18 is a proximal elevational view of the base member and mounting block of the cutting jig of FIG. 13.
Figure 19:
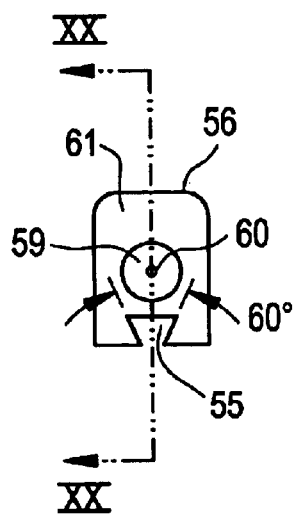
FIG. 19 is a distal elevational view of the measuring block of the cutting jig shown in FIG. 13.

As can be seen, for example, from the view of the distal surface 61 of measuring block 56 shown in FIG. 19 and the view from the proximal end 64 of base member 52 illustrated in FIG. 18, the bottom surface of measuring block 56 has a groove 55 formed therein having a cross-sectional shape corresponding with the cross-sectional shape of rail 51. Measuring block 56 is thereby mounted on base member 52 with groove 55 matingly engaging rail 51 so that measuring block 56 can slide along base member 52.

In the preferred embodiment, the cross-sectional shapes of rail 51 and groove 55 are substantially shaped as inverted triangles to prevent measuring block 56 from being removed from base member 52 during use. However, groove 55 and rail 51 may be formed to have any other alternative mating configuration which allows measuring block 56 to securely engage and slide along rail 51 on base member 52. Other arrangements for slidably mounting the measuring block on the base member may be used. For example, the rail may be formed on the measuring block and the groove may be formed on the base member, or the measuring block may be mounted to the base member by a track formed along the top surface, edges or sides of base member 52.

Base member 52 preferably, though not necessarily, includes a small bore 57 (FIG. 17) formed vertically through rail 51 near the proximal end 64 and into which a stop pin 58 (FIG. 15) is inserted. The stop pin 58 has a length slightly longer than the depth of bore 57 and/or the height of rail 51 so that a portion of the pin 58 protrudes above the upper surface of rail 51, for preventing measuring block 56 from being slid off of rail 51.

Figure 20:
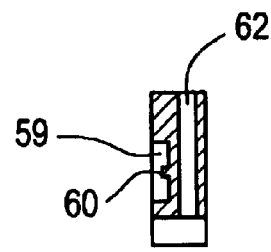
FIG. 20 is a cross-sectional view of the measuring block through the plane XX—XX in FIG. 19.

Referring now to FIGS. 19 and 20, measuring block 56 includes a circular recess 59 formed at the distal face 61 thereof. Recess 59 has a diameter and depth sized to comfortably accept the head 15, 25 of a correspondingly sized fixation screw 10, 20 described above. A protruding nub 60 is formed at the center of recess 59 to engage the central bore 19 formed at the proximal face of the head of the fixation screw. Together, recess 59 and nub 60 thus serve to securely hold and position the head of a fixation screw during the measuring and cutting process.

Figure 15:
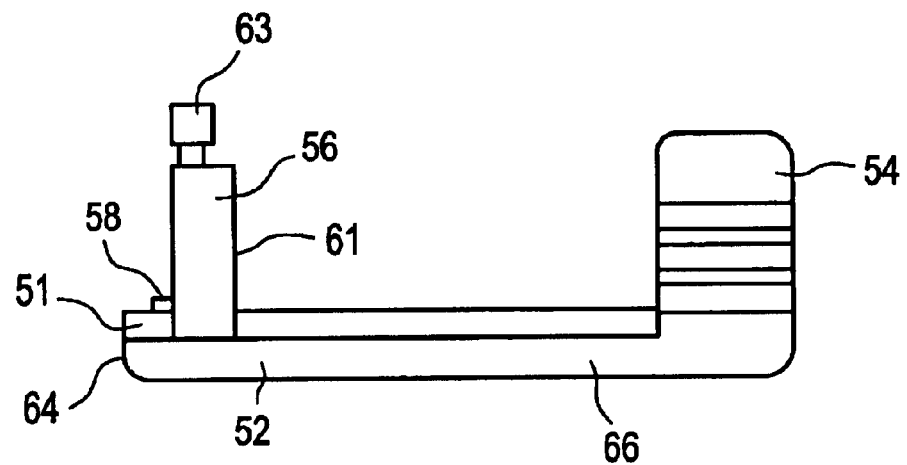
FIG. 15 is a right side elevational view of the cutting jig shown in FIG. 13.

Measuring block 56 also includes a threaded bore 62 extending vertically therethrough proximally to recess 59, for receiving the shaft of thumbscrew 63, shown in FIG. 15. Thumbscrew 63 serves to fix the position of measuring block 56 relative to base member 52 once measuring block 56 is slid along rail 51 to a desired position. Specifically, when the knob of thumbscrew 63 is turned in the clockwise direction, the engagement between the threads in bore 62 and on the thumbscrew causes the bottom of the thumbscrew shaft to contact and then push against the rail 51. Also, once the bottom of the thumbscrew shaft contacts the rail, further rotation of the thumbscrew knob causes an upward pressure to be exerted on measuring block 56. In the preferred embodiment, the inverted triangular cross-sectional shape of groove 55 and rail 51 serves to enhance the locking of the measuring block 56 at the desired position along rail 51.

Figure 17:
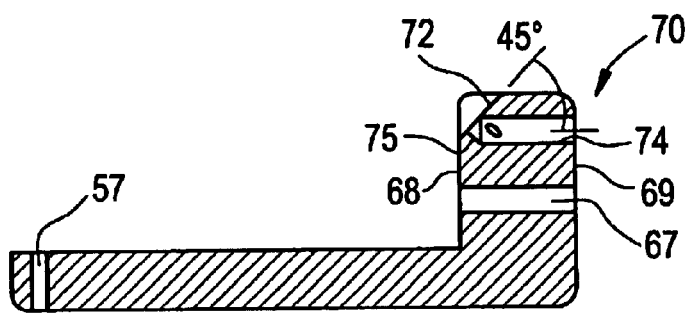
FIG. 17 is a cross sectional view of the base member and mounting block through the plane XVII—XVII in FIG. 16.

Mounting block 54 is provided at the distal end of base member 52, and is preferably integrally formed with base member 52. Rail 51 extends along the upper surface 65 of base member 52 from the proximal end 64 thereof to the proximal face 68 of mounting block 54. As shown in FIGS. 17 and 18, mounting block 54 includes a bore 67 extending horizontally from the proximal face 68 thereof through the distal face 69 thereof. Bore 67 is aligned with the recess 59 on measuring block 56 when measuring block 56 is mounted on rail 51 on base member 52. As with recess 59 in measuring block 56, the diameter of bore 67 through mounting block 54 is just greater than the major diameter of the corresponding fixation screw so as to allow the screw body to comfortably slide through the bore 67.

Figure 16:
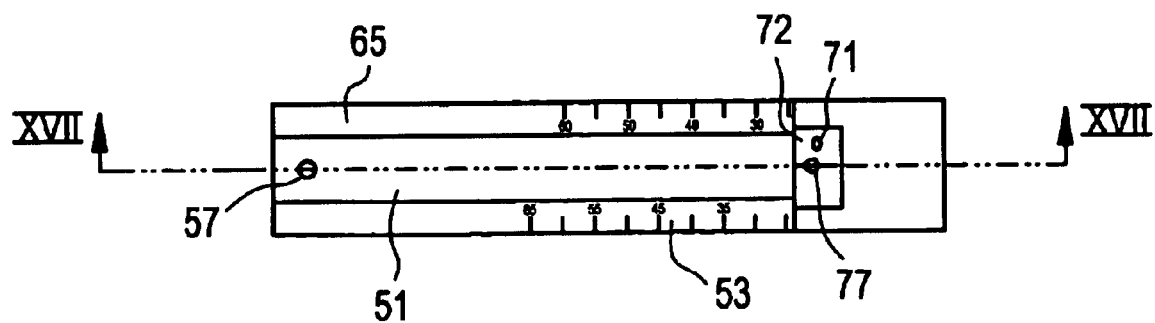
FIG. 16 is a top view of the base member and mounting block of the cutting jig of FIG. 13.

As seen in FIG. 16, a measuring scale 53 is provided on the base member 52 for guiding the measuring process. Scale 53 may be provided on the top surface 65 of base member 52 along one or both sides of rail 51, or may be provided on the side surfaces 66 thereof. The markings of the scale preferably indicate millimeters, although other measurement scales may be used instead, and the markings are labeled to indicate the distance from the distal face 69 of measuring block 56 to the face of the circular recess 59. In other words, the markings indicate the distance from the distal face 69 of measuring block 56 to the marking itself, offset distally by the depth of circular recess 59.

Figure 22:
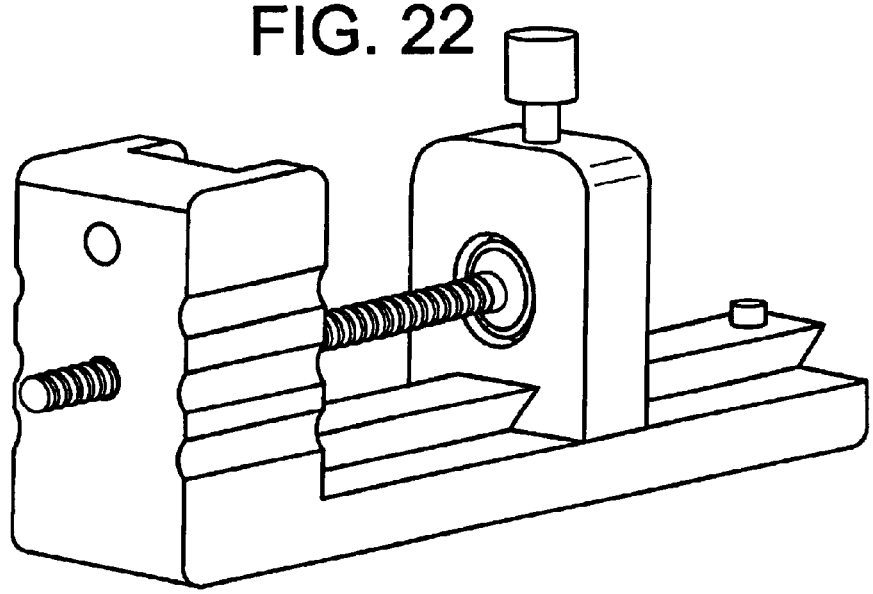
FIG. 22 is a distal perspective view of the cutting jig of FIG. 13 and including a fixation screw mounted therein to be cut.

According to a method of the present invention, when a selected fracture fixation screw is to be cut to a predetermined length, the fixation screw is mounted in a correspondingly sized cutting jig 50 as described above by positioning the head 15 in recess 59 in measuring block 56 and inserting the body 12, 22 of the fixation screw through the bore 67 in mounting block 54, as illustrated in FIG. 22. With the fixation screw mounted in this manner, the measuring block is slid along rail 51 until the distal face 61 of measuring block 56 is aligned with the scale marker or position indicating the desired finished length of the fixation screw. The thumbscrew is then tightened to fix the measuring block 56 in place, and the portion of the screw extending beyond the distal face 69 of mounting block 54 can be cut off to yield the desired length. The excess distal portion of the fixation screw may be cut using bone cutting forceps or a sharp blade, taking care to cut the screw against or as close as possible to the distal face 69 of mounting block 54.

After cutting, the pointed distal tip 16 originally formed at the distal end of the fixation screw is gone, leaving a blunt distal end. It is very difficult to advance a blunt-tipped fixation screw into bone, and risks damaging both the bone and the fixation screw. Thus, it is necessary to recreate the pointed tip at the distal end of the cut fixation screw. For this purpose, a tip sharpener 70 is provided in mounting block 54.

Figure 14:
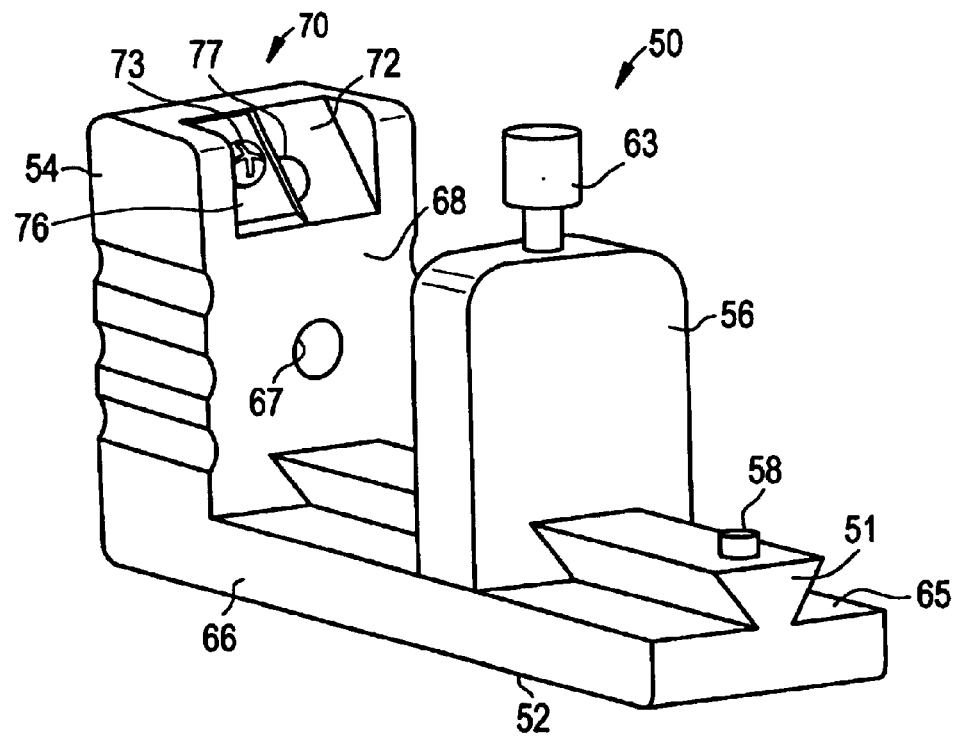
FIG. 14 is a proximal perspective view of the cutting jig shown in FIG. 13.

In the preferred embodiment, tip sharpener 70 includes an angled face 72 formed at the proximal face 68 of mounting block 54, as shown in FIGS. 14, 17 and 18. More specifically, angled face 72 slopes distally and upwardly from the upper central portion of proximal face 68 of mounting block 54, as if a wedge had been removed from the upper proximal edge of mounting block 54.

A sharpening bore 74 is formed in mounting block 54 extending from the distal face 69 of mounting block 54 and extending proximally and parallel to bore 67 for measuring and cutting a fixation screw. Sharpening bore 74 has the same diameter as measuring and cutting bore 67, and is similarly sized to accommodate the fixation screws correspondingly sized for the bore 67. Sharpening bore 74 is tapered at is proximal end 75 according to the shape of a pointed distal tip sought to be achieved by sharpening the blunt distal end of a cut fixation screw. The upper portion of tapered proximal end 75 forms an opening 77 at the angled face 72.

Figure 21:
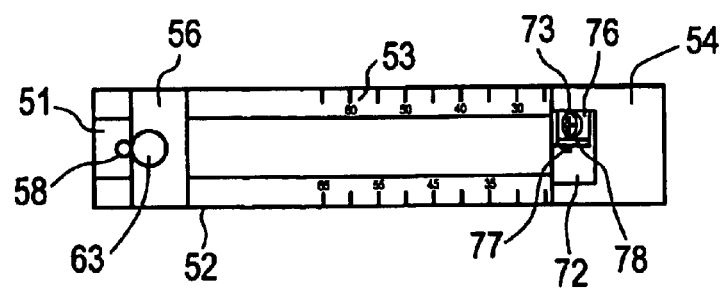
FIG. 21 is a top view of the cutting jig shown in FIG. 13.

As shown in FIG. 21 from a top view of the cutting jig assembly 50, a sharpening blade 76 is affixed to the angled face 72 with a screw 73 driven into screw hole 71 (FIG. 18) formed near exit opening 77 of sharpening bore 74. Sharpened edge 78 of blade 76 covers a part of exit opening 77 so as to shave off material from the distal end of a fixation screw inserted into sharpening hole 74 and turned in the clockwise direction until the tip has been restored. When a fixation screw is inserted into the sharpener 70, the blade 76 will only shave off material from the blunt distal end until the desired pointed tip has been achieved, at which point the distal tip abuts and spins against the tapered end 75 of bore 74 without feeding additional fixation screw material into contact with the sharpened edge 78 of blade 76.

Figure 23:
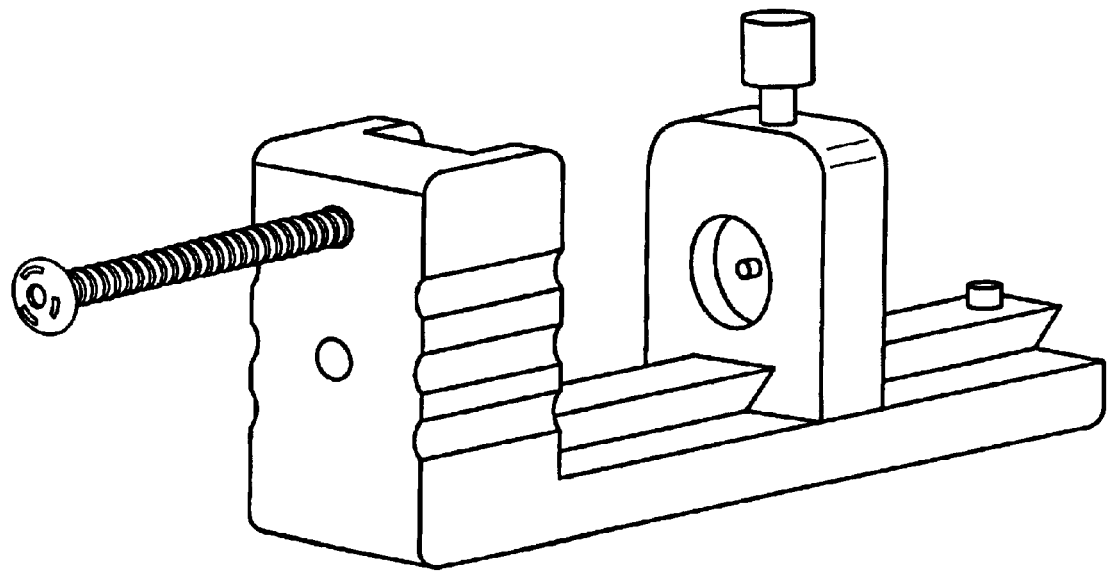
FIG. 23 is a distal perspective view of the cutting jig of FIG. 13 and including a fixation screw inserted into the sharpener.
Figure 24:
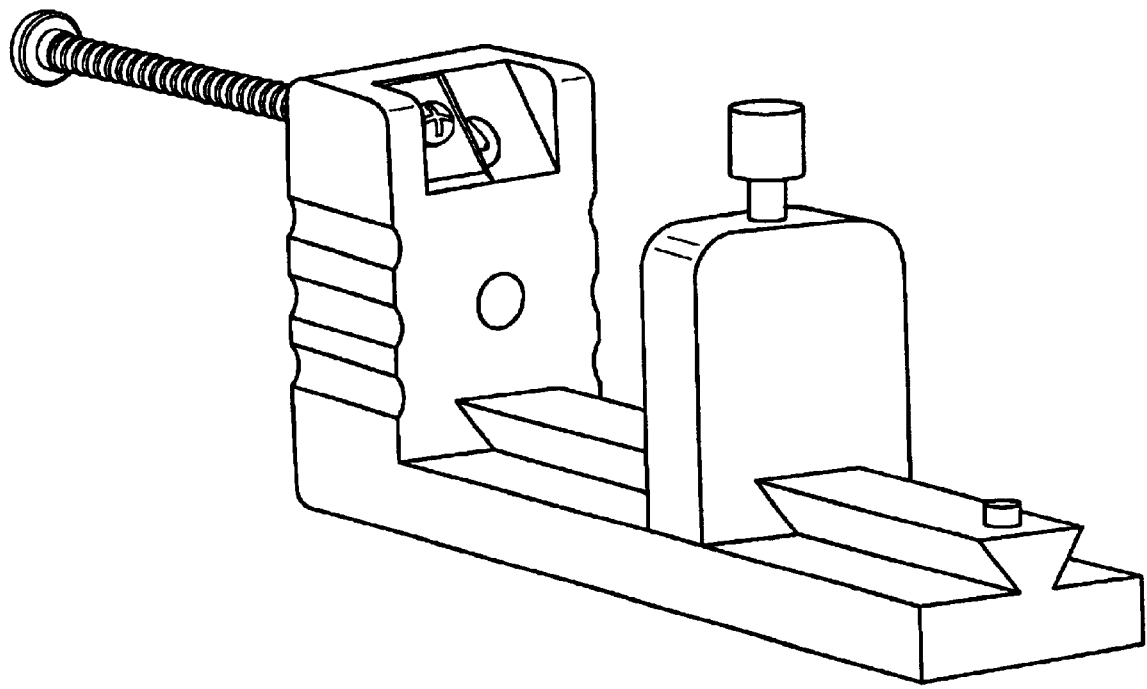
FIG. 24 is a proximal perspective view of the cutting jig and screw in the sharpener shown in FIG. 23.

Thus, after cutting a fixation screw using the cutting jig 50 as described above, the blunt distal end of the cut fixation screw is inserted into sharpening bore 74 at the distal face 69 of the mounting block 54, as shown in FIG. 23. With the aid of a driver for the fixation screw or forceps to hold the screw, for example, the fixation screw is then turned one or two revolutions or until a pointed tip has been re-formed at the distal end of the fixation screw. Similarly to a manual pencil sharpener, the shavings removed from the fixation screw are expelled from the sharpener 70 through the exit opening 77 (see FIG. 24). Typically, once the tip has been recreated, the newly reformed tip abuts against the tapered end 75 of sharpening bore 74.

Preferably, the cutting jig 50 is made of a metal material, such as aluminum or stainless steel. Alternatively, cutting jig 50 may be made of a resinous or polymeric material, such as a plastic. Thumbscrew 63 and sharpening blade 76, however, should be made of stainless steel.

Of course, the cutting jig described herein may be used to revise the length of any other type of fixation element having a relatively constant diameter at least for the distal portion thereof, and which can be reasonably cut using a tool or instrument available to a surgeon.

Figure 25:
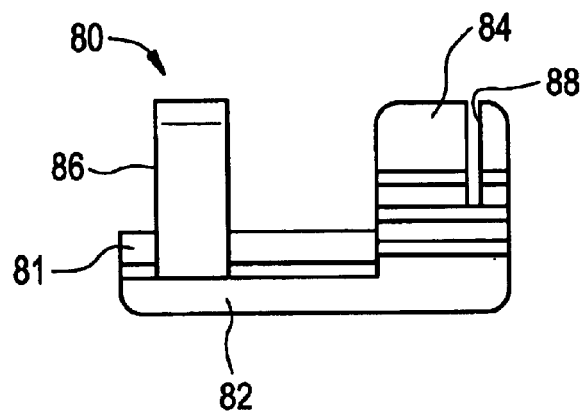
FIG. 25 is a right side elevational view of a second preferred embodiment of a cutting jig in accordance with the present invention.
Figure 26:
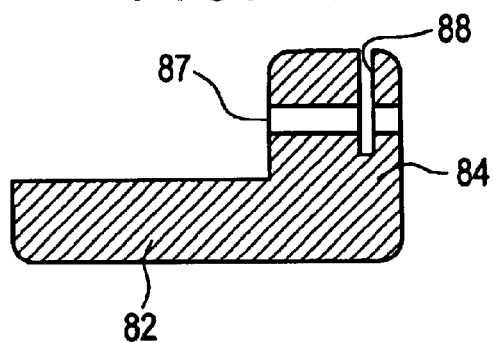
FIG. 26 is a cross-sectional view of the base member and mounting block of the cutting jig shown in FIG. 25.
Figure 27:
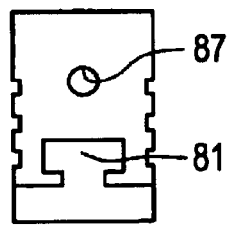
FIG. 27 is a proximal elevational view of the base member and mounting block of the cutting jig shown in FIG. 25.
Figure 28:
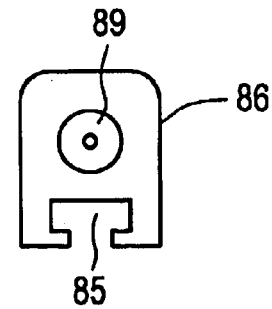
FIG. 28 is a distal elevational view of the measuring block of the cutting jig shown in FIG. 25.

A second preferred embodiment of the cutting jig assembly 80 is shown in FIG. 25 and includes a base member 82, a cutting block 84 and a measuring block 86. A rail 81 is formed on the upper surface of base member 82 for slidably engaging groove 85 formed along the bottom surface of measuring block 86. As illustrated in FIGS. 27 and 28, the cross-sectional shape of rail 81 and groove 85 is T-shaped, and is one example of an alternative mating arrangement to that discussed above and shown in FIGS. 18 and 19.

Measuring block 86 has a recess 89 and a central nub for receiving the head 15 of a fixation screw to be cut. Also, mounting block 84 includes a bore 87 formed horizontally therethrough through which the body of a fixation screw can be inserted while being measured and cut. Unlike in the first embodiment discussed above, however, cutting block 84 also includes a cutting slot 88 which intersects and extends through bore 87 through which a screw body is to be inserted. Cutting slot 88 thus guides a cutting blade when cutting a fixation screw inserted through bore 87, to thereby ensure a straight cut.

Assembly 80 is much simpler in design relative to assembly 50 discussed above. For example, assembly 80 does not include a protruding stop member provided on rail 81, although one may be provided if desired, and also does not include a tip sharpening assembly as is the case in the first embodiment. Here, the tip sharpener is provided separately from the measuring and cutting assembly 80, and is similar to a simple manual pencil sharpener as known in the art. Such design reduces the complexity of assembly 80, which may reduce production costs.

Like the cutting jig 50, the cutting assembly 80 is preferably made of a metal material such as aluminum or stainless steel, or may be made of a resinous or polymeric material such as a plastic. Again, the thumbscrew and sharpening blade on the sharpener, however, should be made of stainless steel. Also, the cutting jig described herein may be used to revise the length of any other type of fixation element having a relatively constant diameter at least for the distal portion thereof, and which can be reasonably cut using a tool or instrument available to a surgeon.

Figure 29:
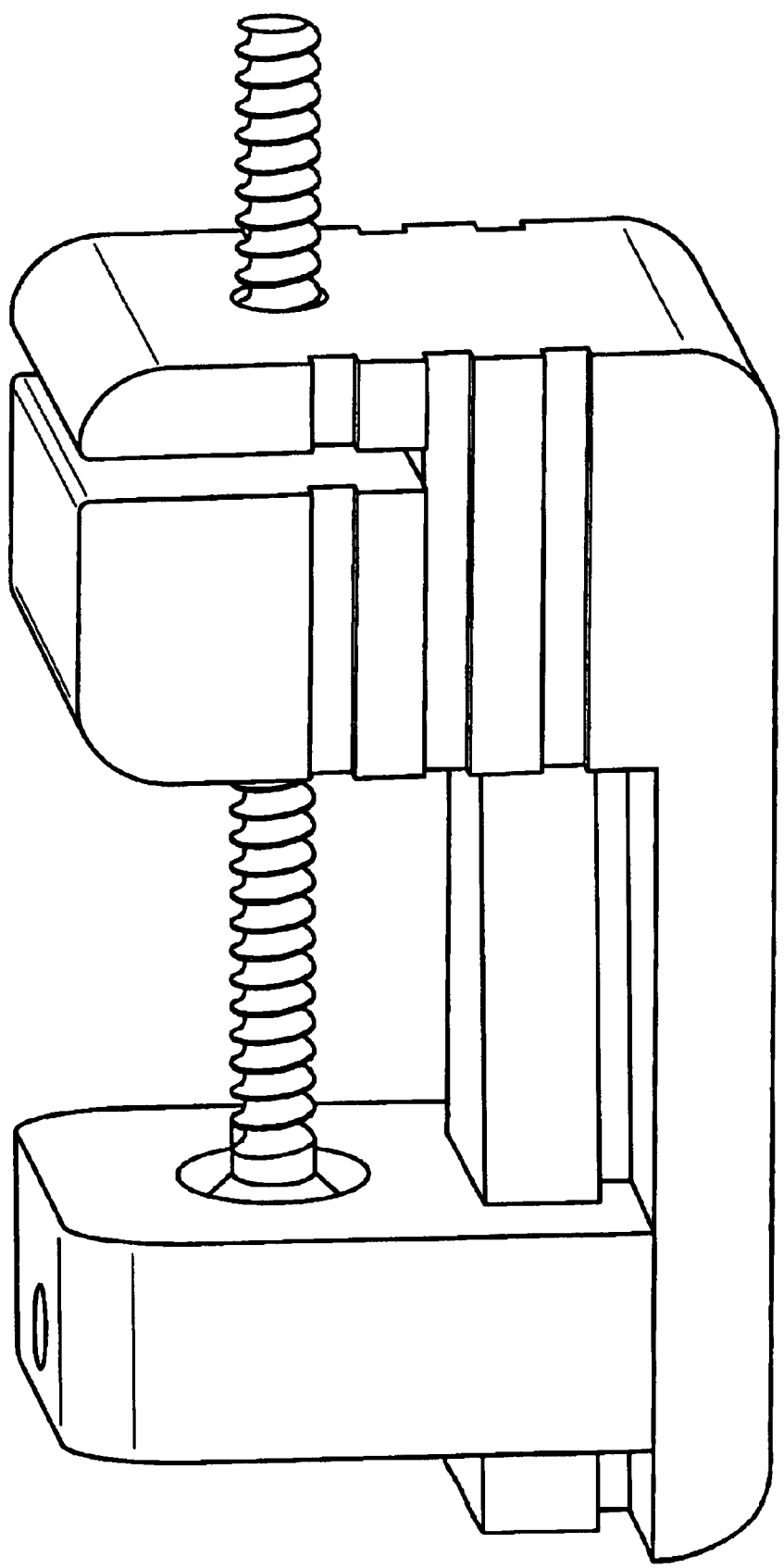
FIG. 29 shows a perspective view of a fixation screw mounted in the cutting jig of FIG. 25.

The steps for using the measuring and cutting assembly 80 are very similar to those described above with reference to the assembly 50 described above. Specifically, when a selected fracture fixation screw is to be cut to a predetermined length, the fixation screw is mounted in a correspondingly sized cutting jig 80 as described above by positioning the head 15 in recess 89 in measuring block 86 and inserting the body 12, 22 of the fixation screw through the bore 87 in mounting block 84, as illustrated in FIG. 29. With the fixation screw mounted in this manner, the measuring block is slid along rail 81 until the distal face of measuring block 86 is aligned with a scale marker or position (not shown) on base member 82 indicating the desired finished length of the fixation screw. A thumbscrew (not shown), which is inserted into a bore extending vertically through the measuring block 86 in a manner similar to the thumbscrew arrangement in the first embodiment, is then tightened to fix the measuring block 86 in place. Subsequently, the portion of the screw extending into and distally beyond the cutting slot 88 is cut off to yield the desired length. The excess distal portion of the fixation screw may be cut using a sharp blade or other cutting tool to cut through the screw body along the cutting slot 88.

Figure 30:
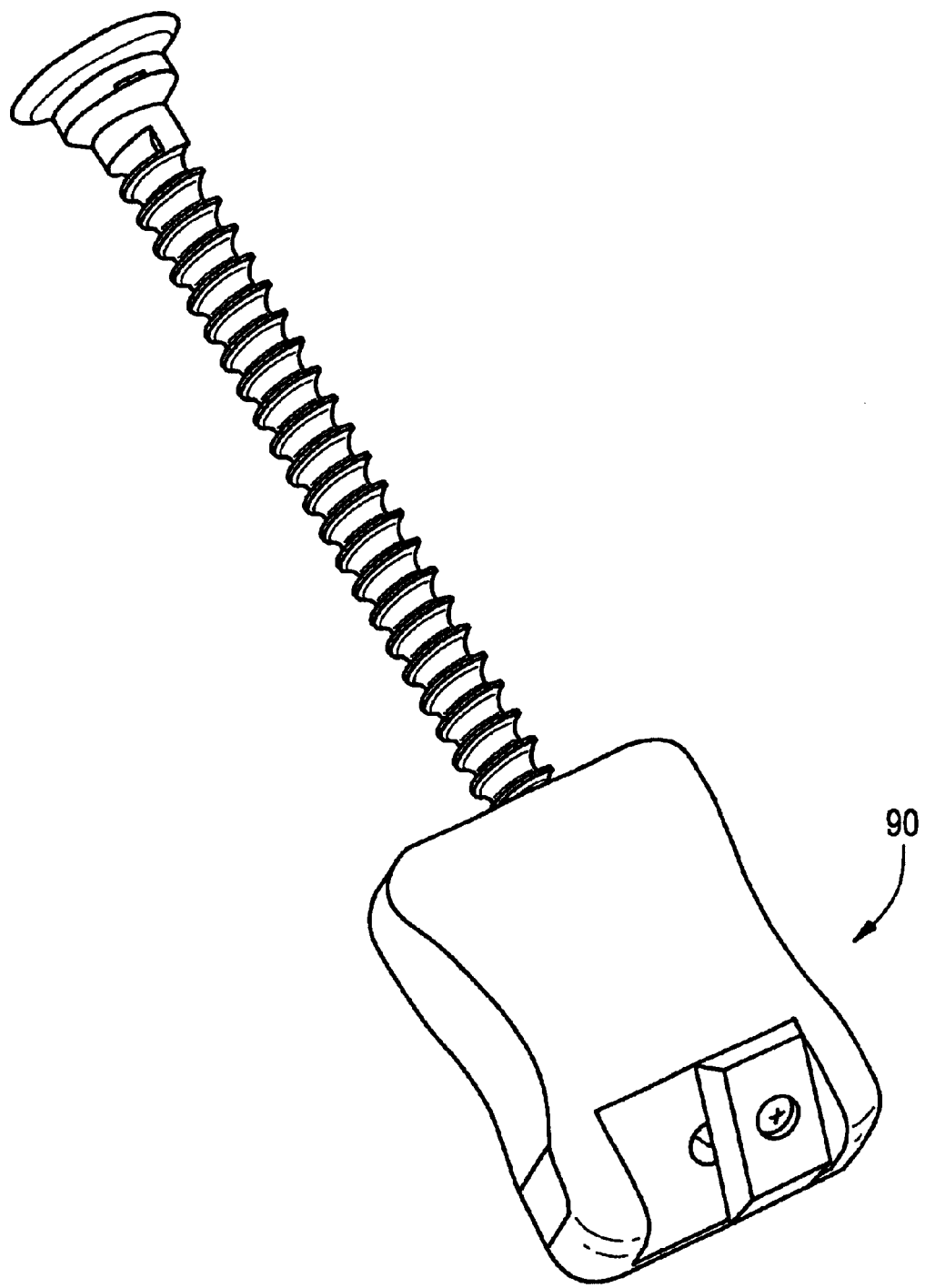
FIG. 30 shows a fixation screw inserted into a sharpener in accordance with the second embodiment of the cutting jig assembly of FIG. 25.

After being cut using the cutting assembly 80, the point at the distal tip must be restored to achieve proper installation into the patient's bone. The blunt distal end of the cut screw is inserted into a sharpener 90, as illustrated in FIG. 30, and the screw is turned in the sharpener until the pointed tip has been restored.

Figure 31:
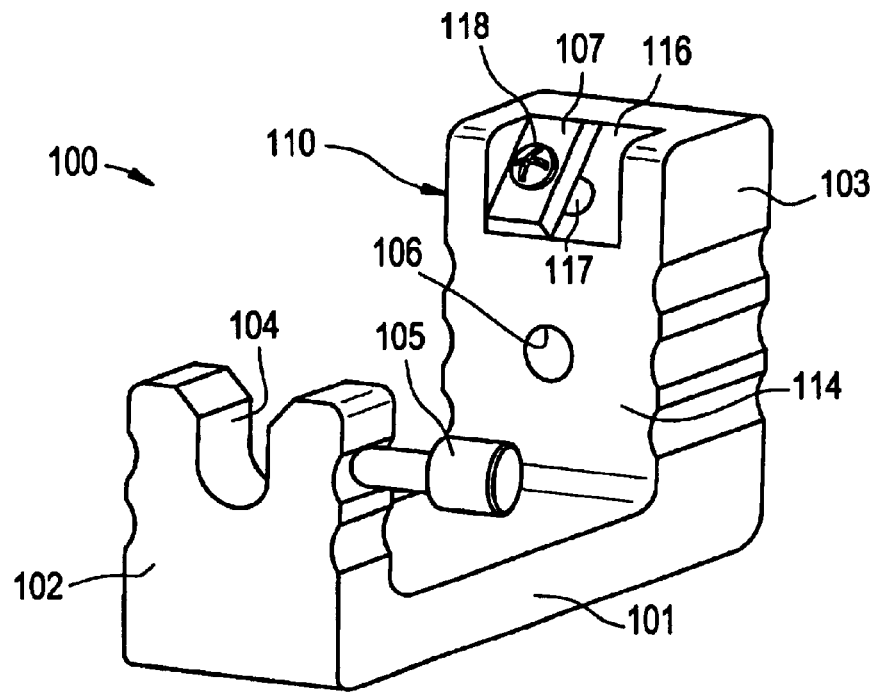
FIG. 31 shows a proximal perspective view of a third preferred embodiment of a cutting jig in accordance with the present invention.
Figure 32:
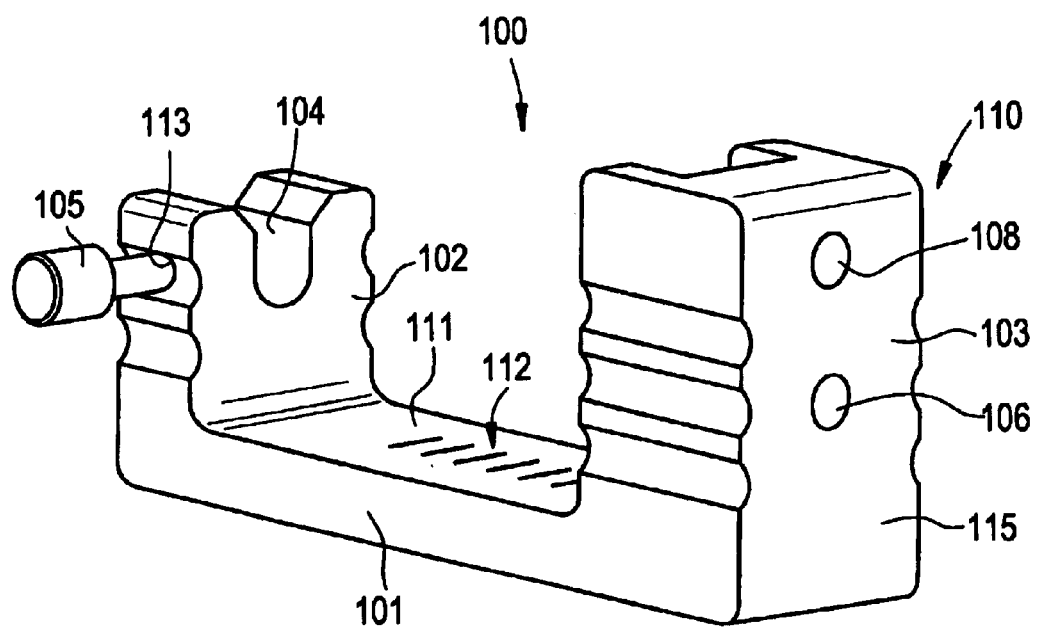
FIG. 32 shows a distal perspective view of the cutting jig shown in FIG. 31.

FIGS. 31 and 32 illustrate a third preferred embodiment of a cutting jig 100 in accordance with the present invention and which includes a base 101, a holding block 102 and a mounting block 103. Holding block 102 is preferably integrally formed at the proximal end of base 101, while mounting block 103 is preferably integrally formed at the distal end of base 101. Cutting jig 100, like the cutting assemblies of the first and second preferred embodiments discussed above, is provided in a plurality of sizes corresponding with the diameters of fixation screws.

Figure 33:
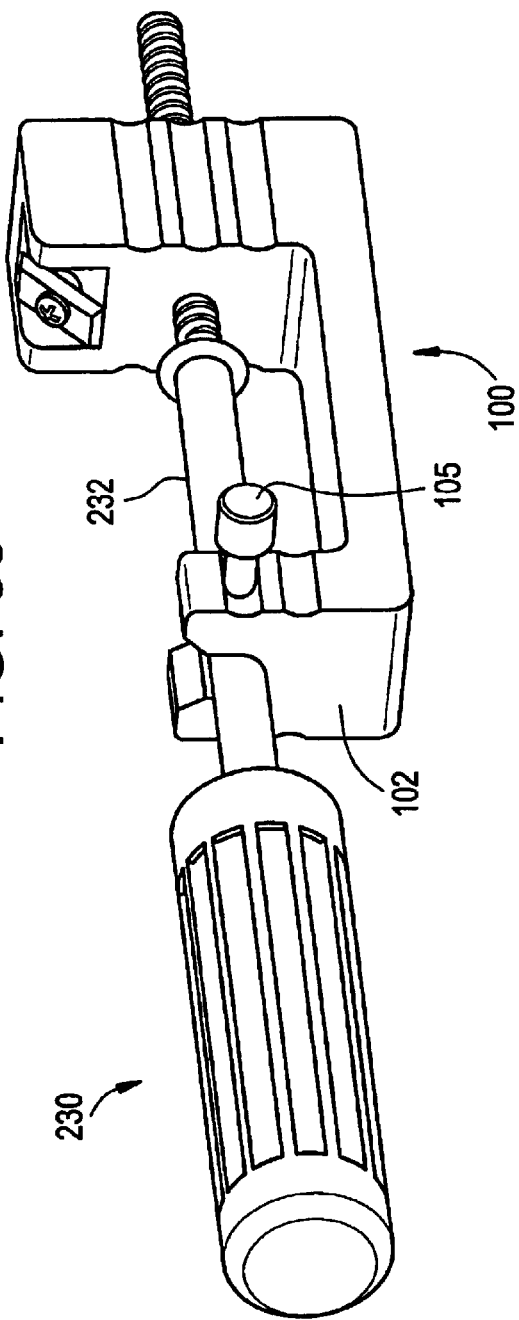
FIG. 33 shows a perspective view of a driver and a fixation screw mounted in the cutting jig of FIG. 31.

Holding block 102 includes a U-shaped seat 104 formed at a top side thereof which is sized and shaped to receive the drive shaft 232 of a driver 230, as shown in FIG. 33. A thumbscrew 105 is provided to extend horizontally through a bore 113 formed through one of the side portions of the holding block 102 and into the space of seat 104, for securing the drive shaft of the driver at a desired position.

Mounting block 103 includes a bore 106 extending horizontally from the proximal face 114 thereof through the distal face 115 thereof, and which is axially aligned with the U-shaped seat 104 such that the axis through the seat 104 as defined by the radius of curvature thereof is coaxial with the axis through the center of bore 106. The diameter of bore 106 is slightly greater than the diameter of the correspondingly sized fixation screw so as to allow the screw body to comfortably slide through the bore 106.

As seen in FIG. 32, a measuring scale 112 is provided on the base 101 for guiding the measuring process. Scale 112 may be provided either on the top surface 111 of base 101 or one or both side surfaces thereof. The markings of the scale preferably indicate millimeters, although other measurement scales may be used, and the markings are labeled to indicate the distance from the distal face 69 to the respective marking.

Cutting jig 100 preferably also includes a tip sharpener 110 provided in mounting block 103, although as in the second embodiment discussed above, the sharpener may be provided as a separate unit from the cutting unit. Similarly to the tip sharpener 70 of the first embodiment, sharpener 110 includes an angled face 116 sloping distally and upwardly from the upper central portion of proximal face 114 of mounting block 103, as if a wedge had been removed from the upper proximal edge of mounting block 103, as shown in FIG. 31. A sharpening bore 108 is formed in mounting block 103 extending from the distal face 115 of mounting block 103 and extending proximally and parallel to bore 106 for measuring and cutting a fixation screw. Sharpening bore 108 has the same diameter as bore 106, and is similarly sized to accommodate the fixation screws correspondingly sized for the bore 106. Sharpening bore 108 is tapered at its proximal end according to the shape of a pointed distal tip sought to be achieved by sharpening the blunt distal end of a cut fixation screw. The upper portion of the tapered proximal end forms an opening 117 at the angled face 116.

A sharpening blade 107 is affixed to the angled face 116 with a screw 118 driven into screw hole (not shown) formed near exit opening 117 of sharpening bore 108. The sharpened edge of blade 107 covers a part of exit opening 117 so as to shave off material from the distal end of a fixation screw inserted into sharpening hole 108 and turned in the clockwise direction until the tip has been restored. When a fixation screw is inserted into the sharpener 110, the blade 107 will only shave off material from the blunt distal end until the desired pointed tip has been achieved, at which point the distal tip abuts and spins against the tapered end of bore 108 without feeding additional fixation screw material into contact with the sharpened edge of blade 107.

To use cutting jig 100 in accordance with the present invention, first, a fracture fixation screw having a desired diameter is selected and the length to which it is to be cut is determined. The appropriate driver is mounted onto the proximal surface of the head of a fixation screw 10, 20, and the body of the fixation screw is mounted in the mounting block 103 by inserting it through the bore 106 from the proximal to distal direction of the cutting jig 100. The position of the fixation screw and driver is adjusted until the proximal surface of fixation screw head 15 is aligned with the scale marker or position indicating the desired length to which the fixation screw is to be cut, as shown in FIG. 33. The thumbscrew 105 is then tightened to fix the driver 230 in place, so that the driver serves to hold the head of the fixation screw in place during the cutting operation. The portion of the screw extending beyond the distal face 115 of mounting block 103 can then be cut off to yield the desired length. The excess distal portion of the fixation screw may be cut using bone cutting forceps or a sharp blade, taking care to cut the screw against or as close as possible to the distal face 115 of mounting block 103.

Figure 34:
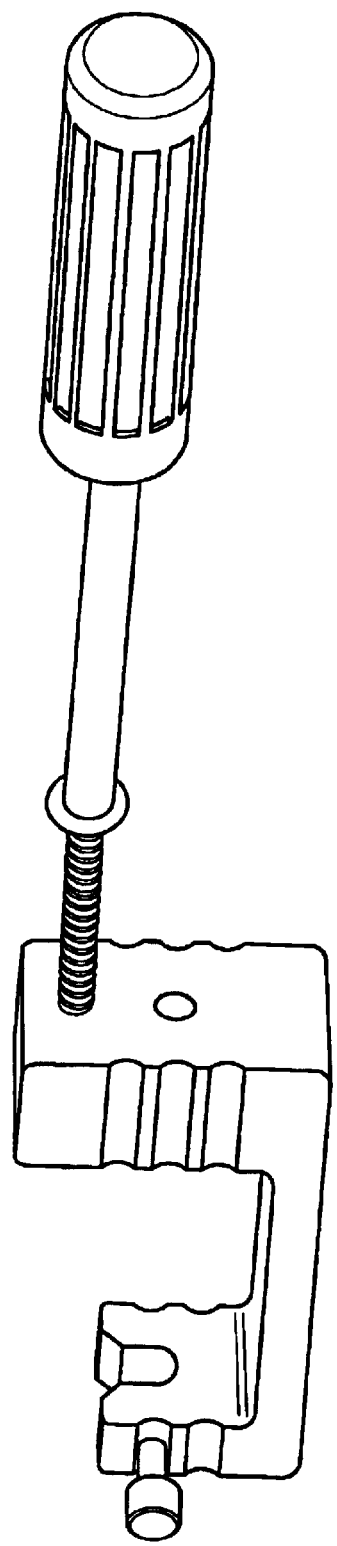
FIG. 34 shows a fixation screw mounted on a driver and inserted into a sharpener incorporated into the cutting jig of FIG. 31.

After cutting a fixation screw using the cutting jig 100 as described above, the blunt distal end of the cut fixation screw is inserted into sharpening bore 108 at the distal face 115 of the mounting block 103, as shown in FIG. 34. With the aid of the fixation driver still or again mounted at the end of the driver 230, the fixation screw is then turned one or two revolutions or until a pointed tip has been re-formed at the distal end of the fixation screw.

Preferably, the cutting jig 100 is made of a metal material such as aluminum or stainless steel, or alternatively, a resinous or polymeric material such as a plastic, while the thumbscrew 105 and the sharpening blade 107, on the other hand, should be made of stainless steel. As with the previous two embodiments, the cutting jig 100 may be used to revise the length of any other type of fixation element having a relatively constant diameter at least for the distal portion thereof, and which can be reasonably cut using a tool or instrument available to a surgeon.

Figure 35:
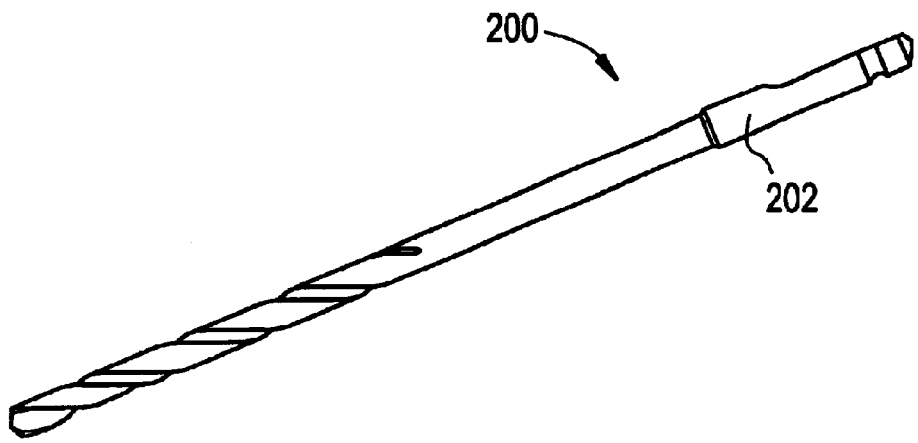
FIG. 35 shows a drill bit usable in conjunction with the present invention.

In performing a fracture fixation procedure in accordance with the present invention using the intraoperatively cut-tolength fixation screws, the surgeon first selects a size (diameter) of a fully threaded fixation screw 10 to be used to secure the bone fracture site. Next, a hole is drilled into the bone across the fracture site at which the fixation screw is to be installed, using a drill bit sized (according to diameter) approximately 70–75% of the diameter of the screw to be inserted, up to a drill bit size of 3.2 mm. An example of a drill bit usable in conjunction with the present invention is shown in FIG. 35, in which the drill bit 200 has a connection fitting formed at the proximal end 202 thereof which enables the drill bit to be releasably engaged with a chuck in a quick-connect and quick-release handle.

Figure 36:
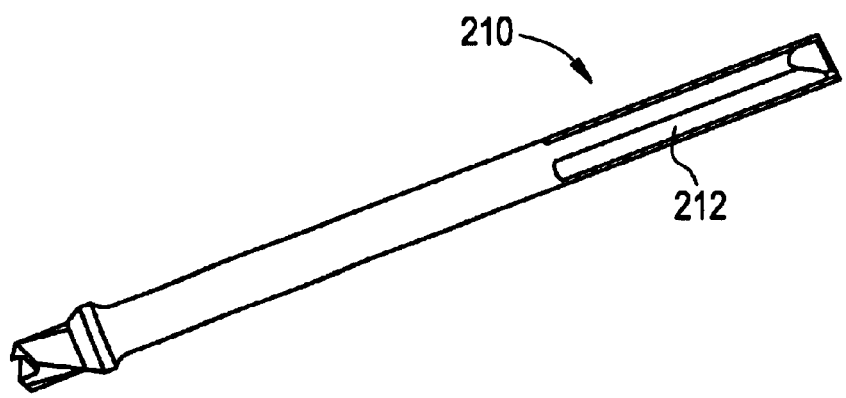
FIG. 36 shows a counterbore drill tip usable in conjunction with the present invention.

After drilling, the hole is countersunk using an appropriately sized counterbore drill tip 210, such as that shown in FIG. 36. The counterbore drill tip should be advanced one to two revolutions or until an adequate recess have been made for the head of the fixation screw. Similarly to the drill bit 200, counterbore drill tip 210 has a proximal end 212 constructed to be releasably engaged with a chuck in a quick-connect handle. Preferably, counterbore drill tip 210 also has a central cannula extending through the length of the drill tip from an opening at the proximal end to an opening at the distal end thereof to thereby receive insertion of a guide pin therethrough to facilitate proper alignment during drilling, if necessary.

A depth guage is then inserted into the drilled hole to determine the length of the screw needed. The tip of the depth gauge should engage the bottom of the drilled hole. The depth of the hole is read to the top of the countersunk hole, or even with the bone surface.

Figure 37:
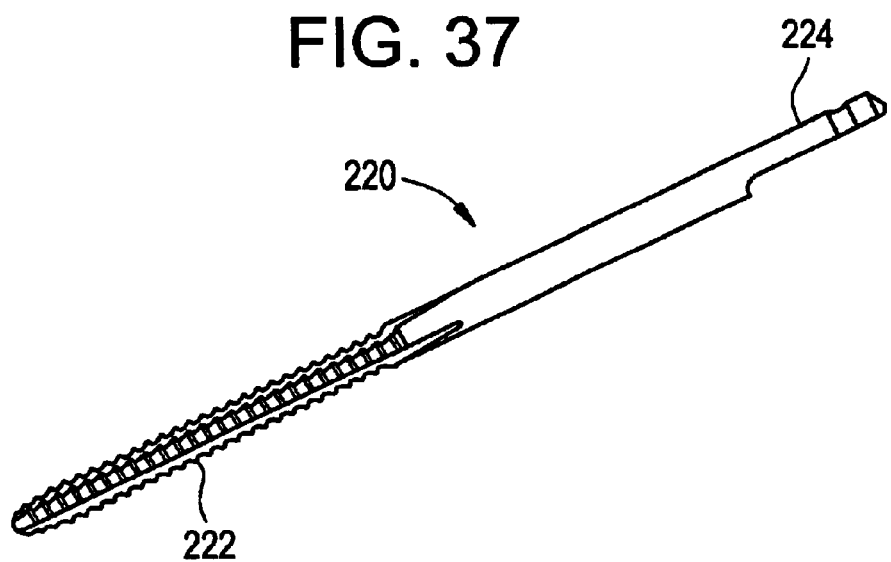
FIG. 37 shows a bone tap usable in conjunction with the present invention.

Next, the drilled hole is tapped using an appropriately sized bone tap for the fixation screw to be inserted. When installing a fixation device into bone, a tap must be used to enable penetration of the fixation screw into the hard bone material. An example of such a tap is shown in FIG. 37, in which tap 220 has a threaded body 222 which is at least as long as the length of the fixation screw to be inserted, so that the entire length of the drilled hole can be tapped. The proximal end of tap 220 may include a quick-connect fitting 224 for being fitted into a quick-connect handle, as is the case for drill bit 200 and counterbore drill bit 210.

Using the cutting jig 50, 80 or 100 as described above, the selected fixation screw is cut to a length corresponding to the depth measurement obtained for the drilled hole in accordance with the procedures described above. After cutting the fixation screw to the desired length, the distal end of the cut screw is sharpened to re-form the tip, using the sharpener 70, 90 or 110 as described above.

The revised screw is then placed onto the end of the appropriately sized driver 230 and aligned with the drilled hole at the fracture site. The driver is rotated to advance the screw into the hole until it is flush with or countersunk with the surface of the bone.

Driver 230 includes a drive shaft 232 which may or may not be cannulated, depending on need for the procedure or if the fixation screw is also cannulated. In the preferred embodiment, the distal end of drive shaft 232 includes three arcuate projections 236 for engaging the arcuate slots 17 formed in the head 15 of the fixation screw (see FIG. 39). If the drive shaft is not cannulated, the distal end of the shaft preferably also includes a protruding nub 238 for engaging the central bore 19 at the proximal face of the head of the fixation screw. This design provides maximum insertion torque while alleviating the potential for stripping the driver coupling structure in the screw. Of course, if the head 15 of the fixation screw is formed with an alternative drive coupling arrangement other than the three arcuate slots 17, the driver 230 is configured to have a matingly shaped drive head.

Preferably, the driver 230 to be used in conjunction with the fixation screw as described above is a torque limiting driver as illustrated in the exploded view of FIG. 38. In addition to the drive shaft 232 having the drive fitting projections 236, driver 230 also includes a handle 234, ratchet gear 231, gear shaft 233, spring 235, and adjustment nub 237. Together, ratchet gear 231, gear shaft 233, spring 235 and adjustment nub 237 operate to limit the amount of torque that is applied to the fixation screw during installation, so as to avoid damaging the screw or the surrounding bone by the exertion of excessive force. Preferably, the torque limit is preset by the manufacturer.

The method described above is repeated for each fixation screw to be inserted.

The present invention also encompasses a variation of the method described above, wherein the lag technique is used to provide additional compression between the fractured bone segments. The method using the lag technique is similar to the fracture fixation procedure described above, except that instead of selecting a fully threaded screw 10, a size of a partially threaded screw 20 is selected. Subsequently, after selection of the appropriate diameter screw to install, a hole is drilled through the proximal bone fragment only using a drill bit 200 corresponding in size to the selected fixation screw. The distal bone fragment is drilled using the smaller drill bit 200 according to the guidelines mentioned above. Another difference between the previously described method and the variation using the lag technique is that only the distal fragment is tapped using the appropriately sized bone tap 220, because the threads on screw 20 are only provided on the distal portion of screw body 22*b* and therefore only engage the distal bone fragment. Thus, the proximal bone fragment is not tapped. In this method, the additional compression is generated by the threaded engagement of the fixation screw in the distal bone fragment and the force of the screw head pressing against the proximal bone fragment.

In both of the methods described herein for bone fracture fixation, washers 30 or 40 may be used in conjunction with the fracture fixation screws 10, 20 to provide additional compression across the fracture fixation site.

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. A method for performing a bone fracture fixation procedure, comprising:

drilling a hole across a bone fracture site;

selecting a fixation screw having a desired diameter;

measuring the drilled hole to determine the necessary length for the fixation screw;

tapping the drilled hole;

cutting the selected fixation screw to the necessary length;

sharpening the distal end of the cut fixation screw to form a pointed tip; and driving the sharpened cut fixation screw into the drilled hole.

2. The method according to claim 1, wherein the selected fixation screw is a fully threaded fixation screw.

3. The method according to claim 1, further comprising attaching a washer around the head of the fixation screw prior to driving the fixation screw into the drilled hole.

4. The method according to claim 1, wherein the fixation screw is made of a bioabsorbable material.

5. The method according to claim 1, wherein the cutting of the fixation screw comprises:
providing a cutting jig which is appropriately sized for receiving the fixation screw, the cutting jig including a base member having a measuring guide, a measuring block slidably mounted on the base member and having a holder sized and shaped for receiving the head of a fixation screw, and a mounting block having a holder for receiving the body of a fixation screw therethrough;
mounting the head of the screw in a holder in the measuring block of the cutting jig;
inserting the body of the screw through the holder in the mounting block;
sliding the measuring block along the base member until the necessary length of the fixation screw is indicated on the measuring guide;
securing the measuring block at the location along the base member at which the necessary length is indicated on the measuring guide;
cutting off any excess length of the fixation screw beyond the necessary length using the mounting block as a cutting guide; and
removing the cut fixation screw from the cutting jig.

6. The method according to claim 5, wherein the sharpening of the cut fixation screw is performed using a sharpener which is integrally formed with the cutting jig.

7. The method according to claim 1, wherein the cutting of the fixation screw comprises:
providing a cutting jig which is appropriately sized for receiving the fixation screw, the cutting jig including a base member having a measuring guide, a holding block at one end of the base member and having a seat sized and shaped for receiving a support element which holds the head of a fixation screw, and a mounting block at the other end of the base member and having a holder for receiving the body of a fixation screw therethrough;
mounting the head of the screw in the support element and placing the support element in the seat in the holding block of the cutting jig;
inserting the body of the screw through the holder in the mounting block;
sliding the support element and fixation screw along the base member and through the seat in the holding block and holder in the mounting block until the necessary length of the fixation screw is indicated on the measuring guide;
securing the support element in the seat when the head of the screw is at the location along the base member at which the necessary length is indicated on the measuring guide;
cutting off any excess length of the fixation screw beyond the necessary length using the mounting block as a cutting guide; and
removing the cut fixation screw from the cutting jig.

8. The method according to claim 1, wherein the sharpening of the cut fixation screw is performed using a sharpener which is integrally formed with the cutting jig.

9. The method according to claim 1, herein the necessary length of the fixation screw is sufficient to span the bone fracture.

10. The method according to claim 9, wherein the screw is a bicortical screw, and the length is sufficient to span the fracture bicortically.

11. A method for performing a bone fracture fixation procedure, comprising:
drilling a hole having a first diameter through a proximal bone fragment at a fracture site;
drilling a second hole concentric with the first hole through a distal bone fragment at the fracture site, the second hole having a second diameter which is less than the first diameter;
selecting a fixation screw having a desired diameter;
measuring the concentric first and second drilled holes to determine the necessary length for the fixation screw;
tapping the second drilled hole;
cutting the selected fixation screw to the necessary length;
sharpening the distal end of the cut fixation screw to form a pointed tip; and
driving the sharpened cut fixation screw into the concentric first and second drilled holes.

12. The method according to claim 11, wherein the selected fixation screw is a partially threaded fixation screw.

13. The method according to claim 11, further comprising attaching a washer around the head of the fixation screw prior to driving the fixation screw into the drilled hole.

14. The method of claim 11, wherein the fixation screw is made of a bioabsorbable material.

15. The method according to claim 11, wherein the cutting of the fixation screw comprises:
providing a cutting jig which is appropriately sized for receiving the fixation screw, the cutting jig including a base member having a measuring guide, a measuring block slidably mounted on the base member and having a holder sized and shaped for receiving the head of a fixation screw, and a mounting block having a holder for receiving the body of a fixation screw therethrough;
mounting the head of the screw in a holder in the measuring block of the cutting jig;
inserting the body of the screw through the holder in the mounting block;
sliding the measuring block along the base member until the necessary length of the fixation screw is indicated on the measuring guide;
securing the measuring block at the location along the base member at which the necessary length is indicated on the measuring guide;
cutting off any excess length of the fixation screw beyond the necessary length using the mounting block as a cutting guide; and
removing the cut fixation screw from the cutting jig.

16. The method according to claim 15, wherein the sharpening of the cut fixation screw is performed using a sharpener which is integrally formed with the cutting jig.

17. The method according to claim 11, wherein the cutting of the fixation screw comprises:
providing a cutting jig which is appropriately sized for receiving the fixation screw, the cutting jig including a base member having a measuring guide, a holding block at one end of the base member and having a seat sized and shaped for receiving a support element which holds the head of a fixation screw, and a mounting block at the other end of the base member and having a holder for receiving the body of a fixation screw therethrough;

mounting the head of the screw in the support element and placing the support element in the seat in the holding block of the cutting jig;

inserting the body of the screw through the holder in the mounting block;

sliding the support element and fixation screw along the base member and through the seat in the holding block and holder in the mounting block until the necessary length of the fixation screw is indicated on the measuring guide;

securing the support element in the seat when the head of the screw is at the location along the base member at which the necessary length is indicated on the measuring guide;

cutting off any excess length of the fixation screw beyond the necessary length using the mounting block as a cutting guide; and removing the cut fixation screw from the cutting jig.

18. The method according to claim 17, wherein the sharpening of the cut fixation screw is performed using a sharpener which is integrally formed with the cutting jig.

19. The method according to claim 11, wherein the necessary length of the fixation screw is sufficient to span the bone fracture.

20. The method according to claim 19, wherein the screw is a bicortical screw, and the length is sufficient to span the fracture bicortically.

* * * * *